United States Patent [19]

Becker et al.

[11] Patent Number: 5,359,116

[45] Date of Patent: Oct. 25, 1994

[54] PROCESS FOR PREPARING TRIMETHYLALUMINUM BY REDUCING METHYLALUMINUM CHLORIDES WITH SODIUM USING HIGH SHEARING FORCES

[75] Inventors: Ralf J. Becker, Hamm; Stefan Gürtzgen, Wuppertal; Jürgen Schneider; Rolf Schrader, both of Unna, all of Fed. Rep. of Germany

[73] Assignee: Witco GmbH, Bergkamen, Fed. Rep. of Germany

[21] Appl. No.: 44,953

[22] Filed: Apr. 9, 1993

[30] Foreign Application Priority Data

May 13, 1992 [DE] Fed. Rep. of Germany ....... 4215745

[51] Int. Cl.$^5$ .............................................. C07F 5/06
[52] U.S. Cl. .................................................. 556/187
[58] Field of Search ........................................ 556/187

[56] References Cited

U.S. PATENT DOCUMENTS

| 2,619,330 | 11/1952 | Willems | 259/96 |
| 2,691,668 | 10/1954 | Ziegler et al. | 260/448 |
| 2,744,127 | 5/1956 | Ziegler et al. | 260/448 |
| 2,839,556 | 6/1958 | Ziegler et al. | 260/448 |
| 3,006,942 | 10/1961 | Nokis | 260/448 |
| 3,268,569 | 8/1966 | Mulder et al. | 260/448 |
| 5,015,750 | 5/1992 | Tran et al. | 556/187 |

FOREIGN PATENT DOCUMENTS

| 2363888 | 7/1975 | Fed. Rep. of Germany . | |
| 734541 | 8/1955 | United Kingdom . | |
| 0822484 | 10/1959 | United Kingdom | 556/187 |
| 0823696 | 11/1959 | United Kingdom | 556/187 |

OTHER PUBLICATIONS

Organometallic Chemistry, H. Zeiss, Reinhold Publishing Corporation, NY, pp. 197–198 (1960).
Inorganic Chemistry and Radiochemistry, H. J. Emeleus, A. G. Sharpe, Academic Press, 1965, p. 269.

*Primary Examiner*—José G. Dees
*Assistant Examiner*—Porfirio Nazario-Gonzalez
*Attorney, Agent, or Firm*—Curtis, Morris & Safford

[57] ABSTRACT

The invention relates to a process for preparing trimethylaluminum from methylaluminum chlorides and sodium in a suspending agent, the reactants being subjected to the shearing action of a rotor-stator machine.

16 Claims, 3 Drawing Sheets

PROCESS FOR PREPARING TRIMETHYLALUMINUM BY REDUCING METHYLALUMINUM CHLORIDES WITH SODIUM USING HIGH SHEARING FORCES

RELATED APPLICATIONS

This application is based upon German Application P 42 15 745.5, filed May 13, 1992, priority of which is claimed and, which is hereby incorporated herein by reference. Reference is also made to concurrently filed application Ser. No. 08/045,973 filed Apr. 9, 1993 in the names of Gürtzgen, Schneider and Schrader, based upon German application P 42 13 202.9 filed Apr. 22, 1992; both of which are hereby incorporated herein by reference.

FIELD OF THE INVENTION

The invention relates to a process for preparing trimethylaluminum from methylaluminum chlorides and sodium in a suspending agent, the reactants being subjected to the shearing action of a rotor-stator machine.

BACKGROUND OF THE INVENTION

Trimethylaluminum (TMA) is increasingly attracting attention because of its many applications in the areas of semiconductors, aluminizing by electrodeposition, and catalysis in polyolefin production.

A great many methods of preparing trimethylaluminum are described in the literature, for example, in U.S. Pat. Nos. 2,744,127 and 2,839,556; Adv. Inorg. Chem. Radiochem. 7, 269 (1967); and Zeiss, Organomet. Chem., ACS Monograph No. 147, 197 (1960).

On the industrial scale, trimethylaluminum is usually produced by reduction of methylaluminum chlorides with molten metallic sodium, dispersed in an inert hydrocarbon such as Tetralin ® (tetrahydronaphthalene), n-decane, n-heptane, etc., according to the reaction equation

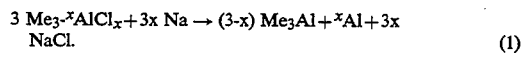

$$3\, Me_{3-x}AlCl_x + 3x\, Na \rightarrow (3-x)\, Me_3Al + {}^xAl + 3x\, NaCl. \quad (1)$$

The methylaluminum chlorides to be used include dimethylaluminum chloride (DMAC) and methylaluminum sesquichloride as well as mixtures thereof.

Because of passivation effects due to the deposition of reaction byproducts (NaCl, Al) on the surface of the sodium, however, the yields are moderate (47 to 85%), and the trimethylaluminum obtained is contaminated by residues of the starting product dimethylaluminum chloride, and of the inert hydrocarbon which is often used in large amounts as a suspending agent.

Using sodium in excess in order that the reaction of the methylaluminum chloride may go to completion will promote the formation of complex alkyls, which reduces the yield still more:

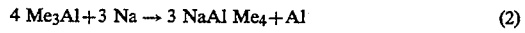

$$4\, Me_3Al + 3\, Na \rightarrow 3\, NaAl\, Me_4 + Al \quad (2)$$

In addition, reactor fouling as well as waste disposal and safety problems due to included sodium are observed.

U.S. Pat. No. 5,015,750 relates to a process by which trimethylaluminum is obtained from methylaluminum chlorides and sodium in yields of about 90% without using sodium in excess. The product contains only about 0.03% chlorine and the synthesis requires considerably less suspending agent than comparable processes. However, such favorable results are obtained only in the presence of from 1 to 10% of catalysts such as alkali-metal and alkaline-earth fluorides, which must also be taken into consideration in connection with waste disposal.

Moreover, in the operating procedure there proposed, dimethylaluminum chloride and sodium are fed in simultaneously, the sodium being directed through the gas space onto the liquid surface. Now if the sodium is distributed by an agitator, for example, over the reactor wall above the liquid surface, the sodium will immediately react with the dimethylaluminum chloride, present in the gaseous phase. With this process repeating itself continually, considerable buildup will occur.

SUMMARY OF THE INVENTION

Surprisingly, it has now been found that practically chlorine-free trimethylaluminum can be obtained in high yields (of about 90%) using relatively small amounts of suspending agents and no catalysts if the reactants are subjected to the shearing action of a rotor-stator machine.

The invention thus relates to a process for preparing trimethylaluminum from methylaluminum chlorides, and preferably dimethylaluminum chloride, and sodium in a suspending agent which is characterized in that the reactants are subjected to the shearing action of a rotor-stator machine.

During their passage through the machine, the reactants are alternately centrifugally accelerated and imparted high peripheral speeds in the rotor slots, then decelerated and directed radially in the next fixed stator slot. In the process, high shearing forces are built up. Because of the rotative speed and the slot configuration, this process occurs so often that particularly good product whirling is achieved and the agglomeration of aluminum and sodium chloride with sodium is prevented.

Additional embodiments of the invention are disclosed in or obvious from the following description and the claims.

DETAILED DESCRIPTION

Figure 1:
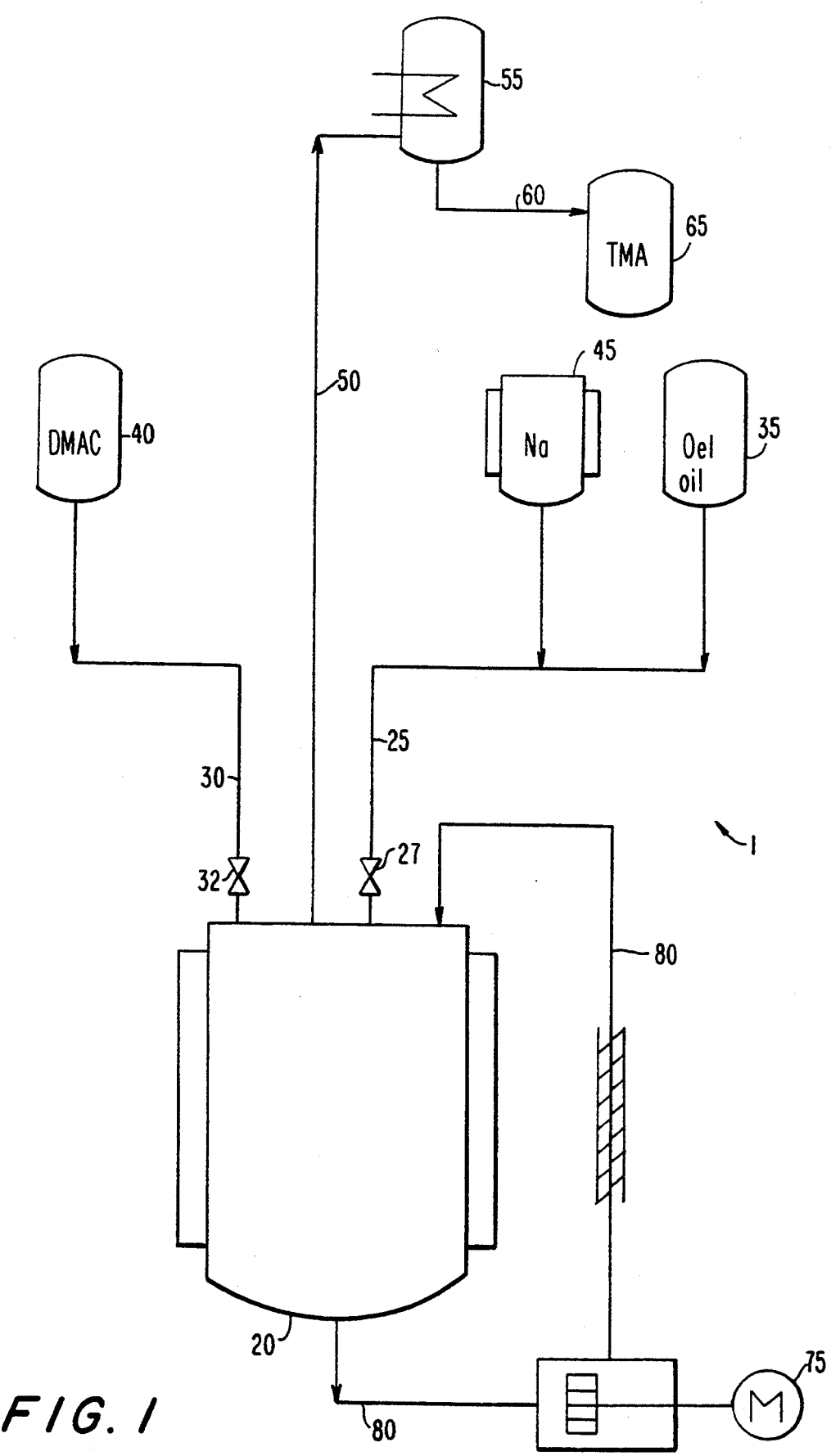
FIGS. 1, 2 and 2 are schematic renderings of embodiments of the invention.
Figure 2:
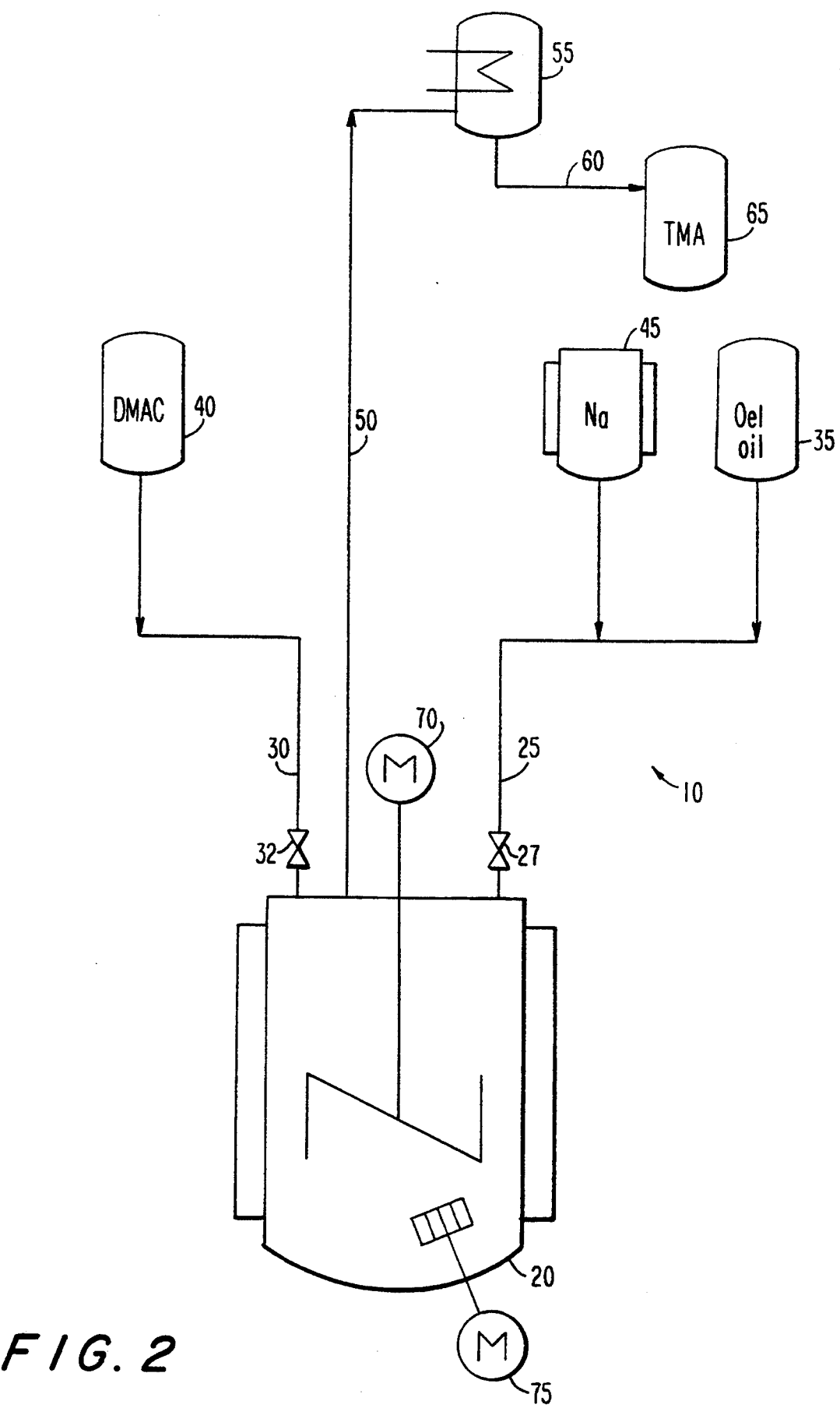
Figure 2A:
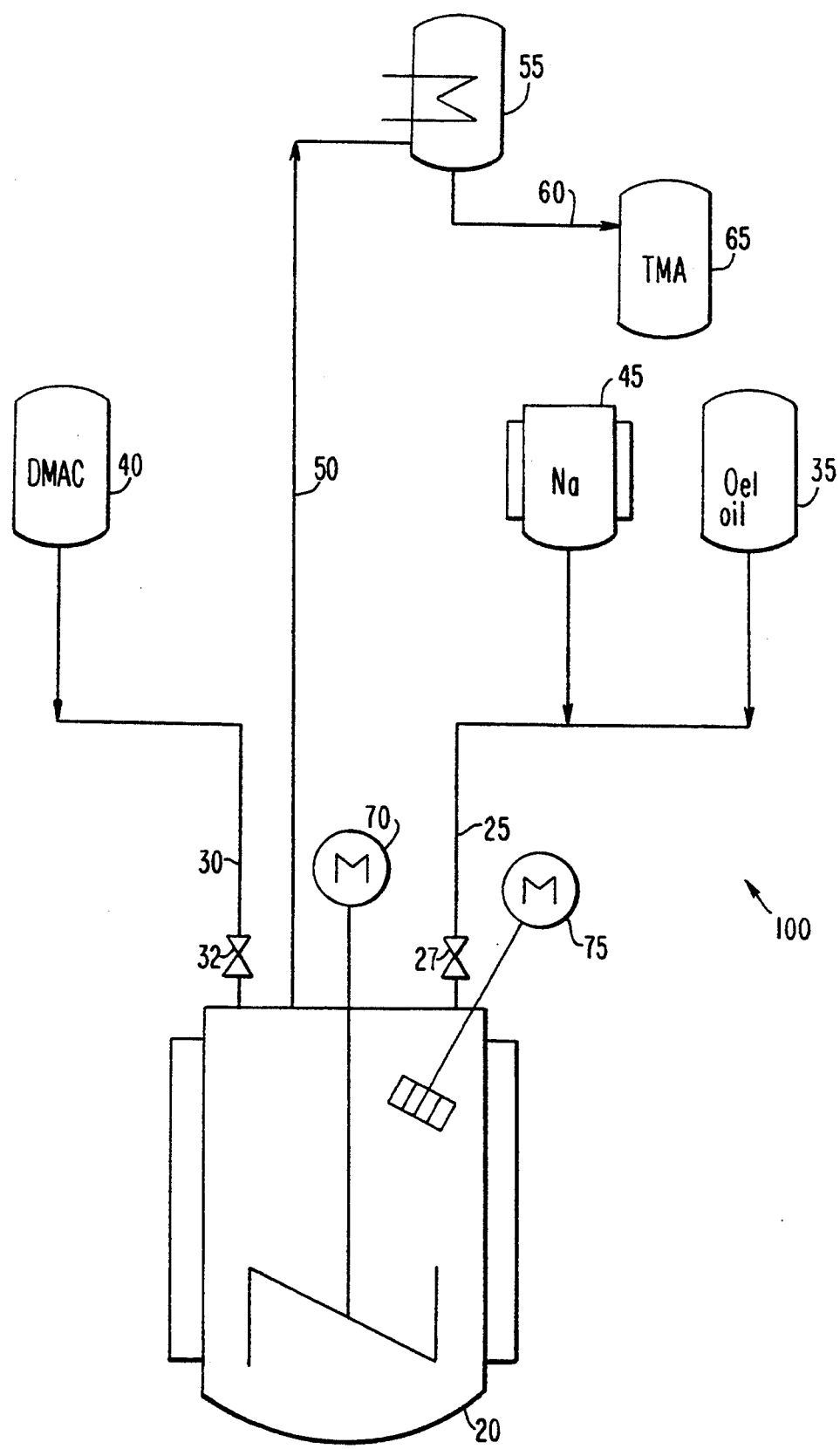

Referring initially to FIGS. 1, 2 and 2a, wherein apparatus 1, 10 and 100, respectively are shown, the apparatus includes: reaction tank 20 into which reactants flow through conduits 25 and 30 from: reactant tanks 35 and 45; and, reactant tank 40, respectively. The methylaluminum chloride, e.g., dimethylaluminum chloride ("DMAC") preferably flows to reaction tank 20 from reactant tank 40 whereas the sodium preferably flows to reaction tank 20 from reactant tank 45 and, oil or toluene or any other suitable suspending agent preferably flows to reaction tank 20 from reactant tank 35. Of course, the order of the reactant tanks can be adjusted by the skilled artisan. Conduits 25 and 30 are preferably equipped with control valves as shown (control valves 27 and 32, respectively).

Product flows from reaction tank 20 through conduit 50 to distillation tank 55 where trimethylaluminum is separated by distillation and sent through conduit 60 to TMA tank 65. The apparatus of each of FIGS. 1, 2 and 2a further includes rotor stator machines ("M") 75. In the apparatus of FIGS. 2 and 2a, rotor stator machine 75 is positioned within reaction tank 20, which is also equipped with stirrer ("M") 70. In the apparatus of FIG. 1, rotor stator machine 75 is positioned in an external loop 80 which flows from the bottom of reaction tank 20 back to the top of it. Of course, if desired, additional instruments can be added to the apparatus of FIGS. 1, 2 and 2a; for instance, reaction tank 20 in the apparatus of FIG. 1 can also include a stirrer, like stirrer 70 of the apparatus of FIGS. 2 and 2a.

Examples of suitable rotor-stator machines for rotor stator machine 75 are:
- SUPRATON ® S300 with conical slot, manufactured by Dorr-Oliver Deutschland GmbH (described in German Patent No. 23 63 888; incorporated herein by reference)
- ULTRA-TURRAX®, manufactured by IKA®, Staufen (described in U.S. Pat. No. 2,619,330 and British Patent No. 734,541; each of which are incorporated herein by reference)
- MISCHSIRENE, manufactured by Fluid, Essen
- DISPAX-REACTOR®, manufactured by IKA®, Staufen (described in U.S. Pat. No. 2,619,330 and British Patent No. 734,541)

The rotor-stator machines may be integrated into a so-called external loop (FIG. 1) or directly into the tank (FIGS. 2 and 2a). The rotor-stator machine is preferably located outside the reaction vessel; for instance, as shown in FIG. 1.

The reaction is preferably carried out at between 130° and 150° C. While lower temperatures ranging from 100° to 130° C. may be used in principle, they are not suitable for a fast reaction, At temperatures above 150° C., a higher pressure will be needed throughout the installation since the reactants dimethylaluminum chloride and trimethylaluminum boil at about 126°-127° C. Above 190° C., the trimethylaluminum will decompose.

For thorough mixing, an additional agitator (stirrer 70, FIGS. 2 and 2a) is used. In addition to intermixing the dimethylaluminum chloride and the suspension present, this agitator will accelerate the removal of heat. Evidently the surface of the sodium used is activated so effectively by the process of the invention that the drawbacks of the prior art which up to now had to be tolerated are prevented and, a number of advantages are obtained, including:

1. High yields of about 90%, based on the dimethylaluminum chloride used, are obtained.
2. The product is nearly free of chlorine (<0.01%) and thus is suitable for use particularly as a catalyst component.
3. The amounts of suspending agent can be kept relatively small.
4. Agglomerations and included sodium, and the attendant handling and waste-disposal hazards, as well as uncontrolled reaction processes, are avoided.

After the reaction, the trimethylaluminum can be separated from the slurry by distillation. The slurries remaining as residues can be handled and worked up safely because of their low sodium content; the hydrocarbons obtained in working up being recycled to the process.

The use of catalysts, such as the alkali-metal or alkaline-earth fluorides suggested in U.S. Pat. No. 5,015,750, is dispensed with.

The remaining residues are worked up for recovery of the hydrocarbons in an aqueous and acidic medium to dissolve the aluminum and the sodium chloride. When alkali-metal or alkaline-earth fluorides are used, the acidic decomposition will result in the production of hydrogen fluoride, for example, in rather high concentrations. This will give rise to severe corrosion problems.

The following examples are given by way of illustration only and are not to be considered as limitations of the present invention, many apparent variations of which are possible without departing from the spirit and scope thereof.

EXAMPLES

Example 1

50 kg of sodium was melted at 130° C. in 250 kg of a high-boiling process oil (Enerpar ® M006 of BP). The mixture was dispersed by means of a Supraton ®. (See FIG. 1.) To the suspension so obtained, 199 kg of DMAC (Cl, 37.5%) was added, and the TMA formed was then separated from the suspension by distillation. (Amount of TMA, 95.4 kg; Al content, 37.2%; Cl, <0.01%; yield, based on TMA, 92%.)

Comparative Example 50 kg of sodium was melted in 250 kg of the process oil. 186 kg of DMAC was then fed into the reactor, bypassing the Supraton ®. Despite a rather high excess of sodium, the reaction did not go to completion. (Cl, 6.7%.)

Example 2

45.4 kg of liquid sodium was added to 225 kg of the process oil. From this coarse suspension, a fine suspension was produced in the Supraton ®, and 185 kg of DMAC was then added. 82.2 kg of TMA (Cl, <0.01%) was obtained. Yield, about 88%, based on TMA.

Example 3

The same procedure was followed as in Example 2, except that the Mischsirene made by Fluid in Essen was used as disperser.

84.1 kg of TMA (Cl, <0.01%) was obtained. Yield, 90%, based on TMA.

Example 4

51.5 g of sodium was dispersed in 401 g of toluene by means of an Ultra-Turrax ®. (FIG. 2.) 210 g of DMAC (96.1%) was then added, with the Ultra-Turrax ® running. A solution of toluene and TMA was distilled off. The yield was 92.5%, based on TMA. Cl content, <0.01%.

Having thus described in detail the preferred embodiments of the present invention, it is to be understood that the invention defined by the appended claims is not to be limited by particular details set forth in the above description as many apparent variations thereof are possible without departing from the spirit or scope of the present invention.

What is claimed is:

1. A process for preparing trimethylaluminum from reactants consisting essentially of methylaluminum chloride and sodium in a suspending agent, the process comprising shearing the reactants by operation of a rotor-stator machine.

2. A process according to claim 1, characterized in that the reactants are in a reaction vessel and the rotor-stator machine is located outside the reaction vessel.

3. A process according to claim 1, characterized in that the reaction is carried out at a temperature between 130° and 150° C.

4. A process according to claim 2, characterized in that the reaction is carried out at a temperature between 130° and 150° C.

5. A process according to claim 1, characterized in that the reactants are in a reaction vessel and the reaction vessel includes an agitator for mixing of the reactants.

6. A process according to claim 2, characterized in that the reactants are in a reaction vessel and the reaction vessel includes an agitator for mixing of the reactants.

7. A process according to claim 3, characterized in that the reactants are in a reaction vessel and the reaction vessel includes an agitator for mixing of the reactants.

8. A process according to claim 4, characterized in that the reactants are in a reaction vessel and the reaction vessel includes an agitator for mixing of the reactants.

9. A process according to claim 1, characterized in that the methylaluminum chloride is dimethylaluminum chloride optionally in admixture with methylaluminum sesquichloride.

10. A process according to claim 2, characterized in that the methylaluminum chloride is dimethylaluminum chloride optionally in admixture with methylaluminum sesquichloride.

11. A process according to claim 3, characterized in that the methylaluminum chloride is dimethylaluminum chloride optionally in admixture with methylaluminum sesquichloride.

12. A process according to claim 4, characterized in that the methylaluminum chloride is dimethylaluminum chloride optionally in admixture with methylaluminum sesquichloride.

13. A process according to claim 5, characterized in that the methylaluminum chloride is dimethylaluminum chloride optionally in admixture with methylaluminum sesquichloride.

14. A process according to claim 6, characterized in that the methylaluminum chloride is dimethylaluminum chloride optionally in admixture with methylaluminum sesquichloride.

15. A process according to claim 7, characterized in that the methylaluminum chloride is dimethylaluminum chloride optionally in admixture with methylaluminum sesquichloride.

16. A process according to claim 8, characterized in that the methylaluminum chloride is dimethylaluminum chloride optionally in admixture with methylaluminum sesquichloride.

* * * * *